United States Patent [19]
Gaglani et al.

[11] Patent Number: 5,938,825
[45] Date of Patent: Aug. 17, 1999

[54] STABILIZED ANTIMICROBIAL COMPOSITIONS CONTAINING HALOPROPYNYL COMPOUNDS

[75] Inventors: Kamlesh D. Gaglani, Belle Mead; Meihua Yang, Bridgewater, both of N.J.

[73] Assignee: Troy Technology Corporation Inc., Wilmington, Del.

[21] Appl. No.: 09/083,015

[22] Filed: May 21, 1998

[51] Int. Cl.$^6$ .................. A01N 47/10; A01N 43/647
[52] U.S. Cl. ................ 106/18.32; 424/405; 514/360; 514/479
[58] Field of Search .............. 106/18.32; 514/478, 514/479, 360; 424/405

[56] References Cited

U.S. PATENT DOCUMENTS

| | | |
|---|---|---|
| 3,660,499 | 5/1972 | Kobayashi et al. . |
| 3,923,870 | 12/1975 | Singer . |
| 4,018,661 | 4/1977 | Cramer et al. . |
| 4,129,521 | 12/1978 | Strobel . |
| 4,259,350 | 3/1981 | Morisawa et al. . |
| 4,276,211 | 6/1981 | Singer . |
| 4,297,258 | 10/1981 | Long, Jr. . |
| 4,552,885 | 11/1985 | Gabriele et al. .................. 514/316 |
| 4,592,773 | 6/1986 | Tanaka et al. . |
| 4,616,004 | 10/1986 | Edwards . |
| 4,639,460 | 1/1987 | Rose . |
| 4,654,434 | 3/1987 | Lang et al. . |
| 4,675,352 | 6/1987 | Winter et al. . |
| 4,710,584 | 12/1987 | Lang et al. . |
| 4,719,227 | 1/1988 | Shade et al. . |
| 4,760,148 | 7/1988 | Seltzer et al. . |
| 4,915,909 | 4/1990 | Song . |
| 4,921,966 | 5/1990 | Steggman et al. . |
| 4,945,109 | 7/1990 | Rayudu . |
| 5,047,571 | 9/1991 | Spang et al. . |
| 5,082,722 | 1/1992 | Gugliemo, Sr. . |
| 5,144,081 | 9/1992 | Heywang et al. . |
| 5,209,930 | 5/1993 | Bowers-Daines et al. . |
| 5,281,645 | 1/1994 | Chicart et al. . |
| 5,342,610 | 8/1994 | Katoh et al. . |
| 5,436,349 | 7/1995 | Winter et al. . |
| 5,468,904 | 11/1995 | Osawa et al. . |
| 5,516,914 | 5/1996 | Winter et al. . |
| 5,554,784 | 9/1996 | Gruening ................ 106/18.32 |
| 5,585,091 | 12/1996 | Pelzer et al. . |
| 5,601,756 | 2/1997 | Swearengin . |

FOREIGN PATENT DOCUMENTS

| | | |
|---|---|---|
| 2138292 | 10/1984 | United Kingdom . |
| 2140299 | 11/1984 | United Kingdom . |

OTHER PUBLICATIONS

Peter D. Gabriele & Robert M. Iannucci, "Protection of Mildewcides and Fungicides From Light Induced Photo-–Oxidation," Journal of Coatings Technology, Federation of Societies For Coatings Technology (Philadelphia, PA, USA), vol. 56 (No. 712), pp. 33–48, (May 19, 1984).

*Primary Examiner*—Anthony Green
*Attorney, Agent, or Firm*—Robert F. Tavares

[57] ABSTRACT

This invention is directed to stabilized antimicrobial compositions which have been stabilized using mixture of at least one halopropynyl compound, and particularly a halopropynyl carbamate fungicide such as IPBC and an effective UV absorber.

19 Claims, No Drawings

STABILIZED ANTIMICROBIAL COMPOSITIONS CONTAINING HALOPROPYNYL COMPOUNDS

BACKGROUND OF THE INVENTION

1. Field of the Invention

The present invention pertains to a stabilized biocidal composition, a paint containing the stabilized biocidal composition, and a method for protecting a substrate from fungal infestation with the stabilized biocidal composition. The stabilized biocidal composition comprises a halopropynyl compound and a UV absorber selected from the group consisting of the esters of 4-alkoxy benzylidene malonic acid, the esters of 2-cyano-3,3-diphenyl acrylate, 3-(4-methylbenzylidene)camhor, 4-alkoxy-2-hydroxybenzophenone, and 2-[2-hydroxy-3-t-butyl-5-(2-octyloxycarbonyl)ethylphenyl]2H-benzotriazole.

2. Description of the Background

Both exterior and interior surfaces, substrates of all types and organic compositions and formulations, when exposed to common environmental conditions, e.g. moisture, are prone to attack, discoloration and various kinds of destruction by a variety of species of microorganisms, including fungi, algae, bacteria and protozoa. As a result, there has always been a great need for effective and economical means to protect, for extended periods of time, commercial compositions and formulations from the deterioration and destruction caused by such microorganisms.

The type of materials which need protection against such microorganisms include, for example, materials such as paints and other coating formulations, surfactants, proteins, starch-based compositions, inks, emulsions and resins, stucco, concrete, stone, and cementaceous surfaces, wood, caulking, sealants, leather, plastics, and textiles. Other important commercial materials such as polymer dispersions or aqueous latex paints containing polyvinyl alcohol, polyacrylates or vinylpolymers, thickener solutions containing cellulose derivatives, kaolin suspensions and metal working fluids, also are prone to degradation by the action of objectionable microorganisms which can significantly impair the usefulness of such compositions. Such degradation may produce, inter alia, changes in pH values, gas formation, discoloration, the formation of objectionable odors, and/or changes in rheological properties.

Wooden objects, for example, are subject to degradation from a wide variety of natural pests. Fungi are particularly prevalent and include brown rots, white rots and soft rots. Fortunately, a variety of compositions have been developed for treating wooden objects and other materials and surfaces to retard the destructive effect of such pests.

A great deal of effort has gone into developing a wide variety of materials which, to various degrees, are effective in retarding or preventing the growth of, and accompanying destruction caused by, such microbes in a variety of circumstances. Such biocidal compounds include halogenated compounds, organometallic compounds, quaternary ammonium compounds, phenolics, metallic salts, heterocyclic amines, formaldehyde donors, organosulfur compounds and the like.

One of the most effective and best known classes of biocides used in such compositions are those containing a halopropynyl moiety, and especially an iodopropynyl moiety. Such compounds are widely disclosed in the patent literature including U.S. Pat. Nos. 3,660,499; 3,923,870; 4,259,350; 4,592,773; 4,616,004 and 4,639,460 to name a few. Included within this class of compounds are the halopropynyl carbamates which are known primarily for their fungicidal activity. Among these is 3-iodo-2-propynyl butyl carbamate, also referred to as IPBC, which is one of the best known and probably the most widely used of the halopropynyl carbamate fungicides. It is a highly active broad spectrum fungicide and, in addition to its fungicidal activity, it has also been associated with algaecidal activity as disclosed in Great Britain Patent 2,138,292 and U.S. Pat. Nos. 4,915,909 and 5,082,722.

Despite their wide acceptance, the halopropynyl carbamate biocides have been reported to be prone to degradation under certain conditions, sometimes resulting in some discoloration and yellowing. In those instances where degradation does occur, and especially in those instances where this degradation results in discoloration and yellowing, the use of such halopropynyl carbamate biocides has been limited, especially in compositions where a white or clear color is desired such as in white caulks, white paints, paper coatings, plastics, plastic coatings and the like.

It has also been suggested that such products may be incompatible with the driers used in certain solvent based systems and that such driers and other potential additives may cause a slow degradation of the biocide.

Each application or system can present its own set of unique conditions and circumstances that may affect the performance of a particular substance and which in turn may require its own unique or specific remedy to insure that acceptable performance is maintained. There is, therefore, a constant need to find improved additives and conditions that will sufficiently inhibit the loss of activity whenever it is necessary to use the antimicrobial under conditions that may pose a threat to its integrity.

A number of attempts to mitigate such problems for a variety of applications have been reported. For example, see Gabriele et al., (U.S. Pat. No. 4,552,885, *Journal of Coatings Technology*, 56(712):33–48), Singer (U.S. Pat. No. 4,276,211) and Long (U.S. Pat. No. 4,297,258). While many of these have found some success in certain applications, none provides a sufficient remedy for all cases. Degradation remains a problem in many instances, therefore, and there is a constant need for new and better remedies.

The present invention provides a significantly more effective way to stabilize halopropynyl compounds, and particularly a halopropynyl carbamate fungicide such as IPBC (known in commerce as Troysan Polyphase®), against the undesirable degradation and yellowing caused by exposure to UV radiation.

SUMMARY OF THE INVENTION

The present invention is directed to a stabilized biocidal composition comprising a halopropynyl compound and a UV absorber selected from the group consisting of the esters of 4-alkoxy benzylidene malonic acid, the esters of 2-cyano-3,3-diphenyl acrylate, 3-(4-methylbenzylidene)camhor, 4-alkoxy-2-hydroxybenzophenone, and 2-[2-hydroxy-3-t-butyl-5-(2-octyloxycarbonyl)ethylphenyl]2H-benzotriazole.

In another embodiment, the present invention is directed to a paint containing the stabilized biocidal composition comprising a halopropynyl compound carbamate and a UV absorber selected from the group identified above.

In yet another embodiment, the invention is directed to a method for protecting a substrate from fungal infestation and yellowing which comprises coating said substrate with an effective amount of a paint containing the stabilized biocidal composition comprising a halopropynyl compound and a UV absorber selected from the group identified above.

DETAILED DESCRIPTION OF THE INVENTION

It has been found that the incorporation of certain UV absorbers into antimicrobial formulations containing, as an active ingredient, an iodo propynyl compound such as IPBC provides an antimicrobial product which is significantly more stable and markedly less prone to degradation and yellowing. The integrity of these iodo propynyl antimicrobial compositions are significantly enhanced by the inclusion of these UV absorbers which act to retard any degradation of the biocide. It is surprising and unexpected that while certain UV absorbers are effective in stabilizing the iodo propynyl antimicrobial compositions, a number of others having closely related structures are not effective.

The class of compounds which can be stabilized in accordance with the present invention are well known and can be generally identified by the following structural formula:

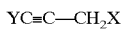

wherein Y is a halogen, preferably iodine and X can be (1) oxygen which is part of an organic functional group; (2) nitrogen which is part of an organic functional group; (3) sulfur which is part of an organic functional group; or (4) carbon which is part of an organic functional group.

The functional group of which oxygen is a part, is preferably an ether, an ester, or a carbamate group. The functional group of which nitrogen is a part is preferably an amine, an amide, or a carbamate group. The functional group of which sulfur is a part is preferably a thiol, a thiane, a sulfone, or a sulfoxide group. The organic functional group of which carbon is a part is preferably an ester, a carbamate or an alkyl group. Examples of active iodopropynyl derivatives are disclosed in U.S. Pat. Nos. 3,923,870; 4,259,350; 4,592,773; 4,616,004; 4,719,227 and 4,945,109, which are herein incorporated by reference. These iodopropynyl derivatives include compounds derived from propynyl or iodopropynyl alcohols such as the esters, acetals, carbamates and carbonates and the iodopropynyl derivatives of pyrimidines, thiazolinones, tetrazoles, triazinones, sulfamides, benzothiazoles, ammonium salts, carboxamides, hydroxamates, and ureas. Preferred among these compounds is the halopropynyl carbamate, 3-iodo-2-propynyl butyl carbamate. This compound is included within the useful class of compounds having the generic formula.

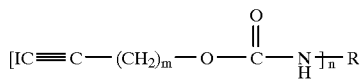

wherein R may have one to three linkages corresponding to n and is selected from the group consisting of hydrogen, substituted and unsubstituted alkyl groups having from 1 to 20 carbon atoms, substituted and unsubstituted aryl, alkylaryl, and aralkyl or from 6 to 20 carbon atoms or cycloalkyl and cycloalkenyl groups of 3 to 10 carbon atoms, and m and n are independently integers from 1 to 3, i.e., they are not necessarily the same.

Particularly preferred are formulations of such halopropynyl carbamates where m is 1 and n is 1 and which have the following formula:

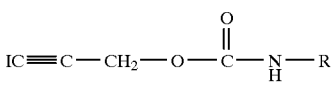

Suitable R substituents include alkyls such as methyl, ethyl, propyl, n-butyl, t-butyl, pentyl, hexyl, heptyl, octyl, nonyl, decyl, dodecyl, and octadecyl; cycloalkyls such as cyclohexyl; aryls, alkaryls and aralkyls such as phenyl, benzyl, tolyl, and cumyl; halogenated alkyls and aryls, such as chlorobenzyl and chlorophenyl; and alkoxy aryls such as ethoxyphenyl and the like.

Especially preferred are such iodopropynyl carbamates as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

There are several criteria that a UV absorber must satisfy in order to provide an antimicrobial that will not degrade or discolor when exposed to sunlight. First it must be compatible with the active halopropynyl antimicrobial under conditions of use. Second, it should be colorless or nearly colorless so as not to impart a color itself. Third it must retain its UV absorbing properties over the period of time that would be required to provide suitable stability to the product in which the antimicrobial is to be used.

It might be expected that any UV absorber should offer some protection against degradation and yellowing caused by UV light. Apparently, however, the effectiveness of a UV absorber to prevent degradation cannot be correlated simply with its ability to absorb light. There must be other significant, though less understood criteria at work which must be satisfied in order to provide adequate protection against the deleterious effects of UV light as is evidenced by the test results.

Among the UV absorbers providing adequate protection are the esters of 4-alkoxybenzylidene malonic acid, 3-(4-methyl benzylidene) camphor, 4-alkoxy-2-hydroxybenzophenones, the esters of 2-cyano-3,3-diphenyl acrylic acid and 2-[2-hydroxy-3-t-butyl-5-(2-octyloxycarbonyl)ethylphenyl]2H-benzotriazole sold under the trademark Tinuvin 384 (Ciba Geigy). (The specific alkoxy group or the alcohol portion of any ester group should not normally affect the UV absorbing properties and/or the stabilizing properties of any of these UV absorbers. It should be understood, however, that the more readily available lower alkyl radicals, especially the methyl, ethyl, propyl and butyl radicals are normally preferred. Similarly the commonly used 2-ethylhexyl alcohol esters common to a number of UV absorbers can also be preferred.)

Preferred UV absorbers are selected from the group consisting of the esters of 4-alkoxybenzylidene malonic acid, 3-(4-methylbenzylidene) camphor and 4-alkoxy-2-hydroxybenzophenones wherein the alkoxy groups are preferably the methyloxy, ethyloxy or propyloxy and the esters are preferably the methyl, ethyl, propyl, butyl and 2-ethylhexyl, esters. (The alcohol portion of the two ester groups on the malonates may be the same or different.)

Especially preferred UV absorbers are dimethyl 4-methoxybenzylidene malonate, diethyl 4-methoxybenzylidene malonate, 3-(4-methylbenzylidene) camphor and 2-hydroxy-4-methoxybenzophenone.

The addition of the UV absorber stabilizes the halopropynyl compounds, particularly halopropynyl carbamate fungicides such as 3-iodo-2-propynyl butyl carbamate (IPBC), in lattices such as acrylic lattices, vinyl acetate acrylic lattices, polyvinyl acetate lattices, styrenated acrylic lattices and styrene butadiene lattices, silicone formulations used for paints and caulks, as well as in leather treatment fluids, other wood treatment formulations and metal working fluids.

In accordance with the invention, the halopropynyl compound can be included in a final formulation for use in such applications as paints, coatings, stucco, plastics, concrete, stone, cementaceous surfaces, wood, caulking, sealants, textiles, and the like, in a broad range from about 0.004% to 5.0% active concentration, more usually in a range from about 0.01% to 2%. Such compositions can be prepared from highly concentrated compositions of the active ingredients by appropriate dilution. The optimum useful range is normally about 0.1% to 1.0% of halopropynyl compound in the final formulations for such end use systems. With the use of such formulations in end use systems, it is possible to protect surfaces as well as other substrates for extended periods of time against microbial growth.

The UV component will normally be added in an amount of from about 10% to 400% by weight of the halopropynyl compound, and more usually from 10% to 300% by weight.

Compositions of the present invention will generally be formulated by mixing the UV components in a selected proportion relative to the halopropynyl compound in a liquid vehicle for dissolving or suspending the active components. The present invention specifically contemplates the preparation of a concentrate containing a liquid vehicle and the above noted constituents. The concentrate is useful for adding a halopropynyl compound into particular formulations in the form of a stabilized biocide. The vehicle also may contain a diluent, an emulsifier and a wetting-agent. As noted above, expected uses of the biocidal compositions include protection of wood, paint, coatings, adhesives, paper, textiles, plastics, cardboard, lubricants, caulking, and the like. An extensive list of potential industries and applications for the present invention can be found in U.S. Pat. No. 5,209,930 which is herein incorporated by reference.

Useful liquid vehicles for the halopropynyl compound, particularly the preferred iodopropynyl butyl carbamate are several glycol ethers and esters like propylene glycol n-butyl ether, propylene glycol tert-butyl ether, 2-(2-methoxymethylethoxy)-tripropylene glycol methyl ether, propylene glycol methyl ether, dipropyleneglycol methyl ether, tripropylene glycol methyl ether, propylene glycol n-butyl ether and the esters of the previously mentioned compounds. Other useful solvents are n-methyl pyrrolidone, n-pentyl propionate and dibasic esters of several dicarboxylic acids and mixtures thereof. Also applicable are ketones including ethyl methyl ketone, 2-octanone and the like.

In many applications, a preferred liquid vehicle for these products can be selected from n-methyl pyrrolidone, propylene glycol n-butyl ether, 1-methoxy-2-propanol, and the dibasic isobutyl ester blend of succinic, glutaric and adipic acids.

When preparing formulations of the present invention for specific applications, the composition also will likely be provided with other adjuvants conventionally employed in compositions intended for such applications such as organic binding agents, additional fungicides, auxiliary solvents, processing additives, fixatives, plasticizers, water soluble or water insoluble dyes, color pigments, siccatives, corrosion inhibitors, antisettlement agents, anti-skinning agents and the like. Additional fungicides used in the composition are preferably soluble in the liquid vehicle.

According to the present invention, substrates are protected from infestation by fungal organisms without yellowing simply by treating said substrate with a composition of the present invention. Such treating may involve mixing the composition with the substrate, coating or otherwise contacting the substrate with the composition and the like.

The following examples are presented to illustrate and explain the invention unless otherwise indicated, all references to parts and percentages are based on weight.

EXAMPLES

In the following examples a styrenated acrylic white house paint was used as the test medium to measure the effect of sunlight on the degradation of IPBC in various IPBC-containing compositions. The composition of the paint is shown in Table 1. The test paint composition was prepared by adding ingredients 2 through 6 slowly to a mixer containing water (ingredient 1). After mixing the composition for about 10 minutes, ingredients 7 through 11 were added, and mixing was continued until a smooth dispersion was obtained. Then the final two ingredients were added. Additional water can be added to obtain a desired viscosity.

TABLE I

FORMULATION OF STYRENATED ACRYLIC WHITE HOUSE PAINT

| No. | Ingredient | Supplier | % W/W |
|-----|------------|----------|-------|
| 1 | Water | | 9.30 |
| 2 | Tamol 850 (30%) | Rohm & Haas | 0.20 |
| 3 | Triton CF-10 | Union Carbide | 0.50 |
| 4 | KTPP | FMC | 0.50 |
| 5 | $NH_4OH$ (7.0%) | | 0.20 |
| 6 | Collateral P:Water (1:1) | BASF | 3.00 |
| 7 | Mineral Spirits | | 1.20 |
| 8 | Texanol | Eastman Chemicals | 0.80 |
| 9 | T102 | Kerr-McGee | 15.00 |
| 10 | Camel White ($CaCO_3$) | Genstar | 26.00 |
| 11 | NytaI 300 | R. T. Vanderbilt | 6.40 |
| 12 | Nopco 8035 | Huls | 0.30 |
| 13 | Acronal 296D | BASF | 36.60 |
| | TOTAL | | 100.00 |

In the following examples, a number of liquid formulations were prepared, each containing (1) 20% by weight Troysan Polyphase® P100 (IPBC), (2) 40% by weight of one of the UV absorber in an amount as indicated in each example which follows, and (3) 40% by weights of N-methyl pyrrolidone as a liquid vehicle. Each was then incorporated into the white test paint by mixing in an amount sufficient to provide a test paint having IPBC present at a level of 0.3%. The paint formulations containing IPBC and UV absorbers were then applied on a Leneta chart with help of a 3 mil Bird type applicator. The paint film was allowed to dry for 10–15 minutes and then sprayed with a clear non-yellowing varnish (~3 mils), namely, Kamar Varnish 1312. The varnish was obtained from Krylon Products Group, The Specialty Division, Division of Sherwin-Williams Company, Ohio. The object of the varnish was to trap any of the chromophores formed during subsequent UV light exposure and to assure a short and reproducible test for accessing light-induced yellowing.

The paint film thus produced was exposed to 340 nm UV radiation for four hours and the yellowing was measured by Microflash 200D or Byk Handy Color measurement device. The difference in yellowing between a blank (the white test paint without fungicide) and the candidate paint sample, $\Delta b$, was recorded and used as the response for each test. A paint formulation, which did not contain any UV absorber additive but which did have the same amount of IPBC as all the other IPBC-containing paint formulations, also was tested and served as the positive control response.

The following examples report the results obtained using several different UV absorbers.

Example 1

The formulation added to the paint contained IPBC but had no UV absorber. The Δb value was 6.9. This Example shows that in the absence of a suitable UV absorber, a significant yellow color develops due to a partial degradation of the IPBC.

Example 2

The Δb value was 2.4 when 3-(4-methyl benzylidene) camphor was used as the UV absorber. This Example shows that there was very little color change when compared to the blank and that the UV absorber was effective in inhibiting degradation of the IPBC.

Example 3

The Δb value was 1.7 when dimethyl 4-methoxy benzylidene malonate was used as the UV absorber. This Example shows that this UV absorber was very effective in inhibiting degradation of the IPBC by UV light. Any color change was barely perceptible to the eye.

Example 4

The Δb value was 16.4 when methyl 2-cyano-3-methyl-4-methoxyphenyl acrylate was used as the UV absorber. This Example shows that this UV absorber, gave very poor results. This result was even worse than the result obtained with no UV absorber (Example 1). The degree of yellowing in this result may have been due, in part, to the fact that the UV absorber itself had a yellow coloring.

Example 5

The Δb value was 4.3 when methyl 2-cyano-3-(4-methoxyphenyl)acrylate was used as the UV absorber. This example shows that while there was some benefit due to the presence of the UV absorber, the degree of yellowing exceeded that which was considered acceptable.

Example 6

The Δb value was 7.9 when dimethyl benzylidene malonate was used as the UV absorber. This amount of yellow color was unacceptable.

Example 7

The Δb value was 2.2 when 4-methoxy-2-hydroxybenzophenone was used as the UV absorber. This Example shows that the UV absorber was effective to inhibit degradation of the IPBC and prevent significant yellowing.

Example 8

The Δb value was 8.0 when 3-(3-hydroxypropyloxy) propyl 2-hydroxy benzoate was used as the UV absorber. This amount of yellow color exceeded by far what was acceptable.

Example 9

The Δb value was 4.5 when 2-ethylhexyl 4-methoxycinnamate was used as the UV absorber. This Example shows that while there was some benefit due to the UV absorber, the degree of yellowing exceeded that which was considered acceptable.

Example 10

The Δb value was 3.5 when 2-[2-hydroxy-3-t-butyl-5-(2-octyloxycarbonyl)ethylphenyl]2H-benzotriazole, sold under the trademark Tinuvin 384 (Ciba Giegy), was used as the UV absorber. While a slight change in color was perceptible, the UV absorber was reasonably effective and the amount of yellowing was acceptable.

Example 11

The Δb value was 4.1 when a UV absorber sold under the trademark Tinuvin 400 (a 1,3,5-triazine derivative sold by Ciba Geigy) was used as the UV absorber. While there was some benefit due to the UV absorber, the degree of yellowing did exceed that which was considered acceptable.

Example 12

The Δb value was 6.6 when a UV absorber sold under the trademark Tinuvin 1130 (a benzotriazole derivative sold by Ciba Geigy) was used as the UV absorber. This resulting yellow color far exceeded what was acceptable.

Example 13

The Δb value was 3.7 when ethyl 2-cyano-3,3-diphenylacrylate was used as the UV absorber. While there was a slight, perceptible change in color, it was considered acceptable.

Example 14

The Δb value was 3.7 when 2-ethylhexyl 2-cyano-3,3-diphenylacrylate was used as the UV absorber. While there was a slight, perceptible change in color, it was acceptable.

Example 15

The Δb value was 4.2 when 4,4'-dimethoxy-2,2'-dihydroxybenzophenone, was used as the UV absorber While there was some benefit due to the UV absorber, the degree of yellowing exceeded that which was considered acceptable.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

We claim:

1. A stabilized biocidal composition comprising an iodopropynyl compound selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate and 3-iodo-2-propynl phenyl carbamate and a UV absorber selected from the group consisting of the esters of 4-alkoxy benzylidene malonic acid, the esters of 2-cyano-3,3-diphenyl acrylate, 3-(4-methylbenzylidene)camphor, 4-alkoxy-2-hydroxybenzophenone, and 2-[2-hydroxy-3-t-butyl-5-(2-octyloxycarbonyl)ethylphenyl]2H-benzotriazole wherein the alkoxy groups are methyl, ethyl, propyl or butyl and the esters can be methyl, ethyl, propyl, butyl or 2-ethylhexyl esters and wherein the ratio of UV absorber to iodopropynyl compound is at least 1:10.

2. The composition of claim 1 wherein the UV absorber is selected from the group consisting of the esters of 4-methoxybenzylidene malonic acid, 3-(4-methylbenzylidene)camphor and 2-hydroxy4-methoxybenzophenone.

3. The composition of claim 2 wherein the iodopropynyl carbamate is 3-iodo-2-propynyl butyl carbamate.

4. The composition of claim 3 wherein the UV absorber is an ester of 4-methoxy benzylidene malonic acid.

5. The composition of claim 4 wherein the UV absorber is an ester of 4-methoxybenzilidenemalonic acid and the two ester groups are alike or different and are either methyl, ethyl, propyl, butyl or 2-ethylhexyl esters.

6. The composition of claim 5 wherein the UV absorber is dimethyl 4-methoxybenzylidene malonate or diethyl 4-methoxybenzylidene malonate.

7. The composition of claim 6 wherein the 3-iodo-2-propynyl butyl carbamate and the UV absorber are present in a proportion of from about 1 part 3-iodo-2-propynyl butyl carbamate to 4 parts UV absorber to about 4 parts 3-iodo-2-propynyl butyl carbamate to 1 part UV absorber.

8. The biocidal composition of claim 7 wherein the 3-iodo-2-propynyl butyl carbamate and the UV absorber are present in a proportion of from about 1 part 3-iodo-2-propynyl butyl carbamate to 2 parts of the UV absorber to about 2 parts 3-iodo-2-propynyl butyl carbamate to 1 part of the UV absorber.

9. The biocidal composition of claim 8 containing from about 5% to 40% of the 3-iodo-2-propynyl butyl carbamate.

10. The composition of claim 3 wherein the UV absorber is 3-(4-methylbenzilidene)camphor.

11. The composition of claim 10 wherein the 3-iodo-2-propynyl butyl carbamate and the UV absorber are present in a proportion of from about 1 part 3-iodo-2-propynyl butyl carbamate to 4 parts UV absorber to about 10 parts 3-iodo-2-propynyl butyl carbamate to 1 part UV absorber.

12. The composition of claim 3 wherein the UV absorber is an ester of 2-cyano-3,3-diphenylacrylate.

13. A paint containing a biocidal composition comprising 3-iodo-2-propynyl butyl carbamate and a UV absorber selected from the group consisting of the esters of 4-methoxy benzylidene malonic acid, 3-(4-methylbenzylidene)camphor and 2-hydroxy-4-methoxy benzophenone wherein the ratio of the UV absorber to 3-iodo-2-propynyl butyl carbamate is at least 1:10.

14. The paint of claim 13, wherein the UV absorber is dimethyl 4-methoxybenzylidene malonate or diethyl 4-methoxy benzylidene malonate.

15. The paint of claim 14 wherein the 3-iodo-2-propynyl butyl carbamate and the UV absorber are present in a proportion of from about 1 part 3-iodo-2-propynyl butyl carbamate to 3 parts UV absorber to about 3 parts of 3-iodo-2-propynyl butyl carbamate to 1 part UV absorber.

16. The paint of claim 15 wherein the paint contains from about 0.1% to about 1.0% of the 3-iodo-2-propynyl butyl carbamate.

17. The paint of claim 13 wherein the UV absorber is 3-(4-methylbenzilidene)camphor.

18. The paint of claim 17 wherein the 3-iodo-2-propynyl butyl carbamate and the UV absorber are present in a proportion of from about 1 part 3-iodo-2-propynyl butyl carbamate to 4 parts UV absorber to about 10 parts of 3-iodo-2 propynyl butyl carbamate to 1 part UV absorber and wherein the paint contains from about 0.1% to about 1.0% of the 3-iodo-2-propynyl butyl carbamate.

19. A method for protecting a substrate from fungal infestation and yellowing which comprises coating said substrate with a paint containing a biocidal composition comprising 3-iodo-2-propynyl butyl carbamate and an ester of 4-methoxybenzylidenemalonic acid in a 4:1 to 1:4 ratio, said 3-iodo-2-propynyl butyl carbamate being present in said paint at a concentration in the range from about 0.1% to 1.0%.

* * * * *